United States Patent [19]

Saito et al.

[11] Patent Number: 5,120,468

[45] Date of Patent: Jun. 9, 1992

[54] 2-SUBSTITUTED-ALKYL ETHER AND LIQUID CRYSTAL COMPOSITION

[75] Inventors: Shinichi Saito; Hiromichi Inoue; Kazutoshi Miyazawa; Kouji Ohno; Makoto Ushioda, all of Kanagawa, Japan

[73] Assignee: Chisso Corporation, Ohsaka, Japan

[21] Appl. No.: 563,801

[22] Filed: Aug. 6, 1990

Related U.S. Application Data

[63] Continuation of Ser. No. 151,501, Feb. 2, 1988, abandoned.

[30] Foreign Application Priority Data

Feb. 2, 1987 [JP] Japan ................................. 62-21963

[51] Int. Cl.$^5$ ..................... C09K 19/34; C07D 239/02
[52] U.S. Cl. ................................. 252/299.61; 544/298
[58] Field of Search ............... 252/299.61; 544/298

[56] References Cited

U.S. PATENT DOCUMENTS

| | | | |
|---|---|---|---|
| 4,576,732 | 3/1986 | Isogai et al. | 252/299.65 |
| 4,613,209 | 9/1986 | Goodby et al. | 350/350.5 |
| 4,614,609 | 9/1986 | Inoue et al. | 252/299.66 |
| 4,654,162 | 3/1987 | Sugimori et al. | 252/299.01 |
| 4,676,925 | 6/1987 | Inoue et al. | 252/299.65 |
| 4,725,688 | 2/1988 | Taguchi et al. | 544/298 |
| 4,744,918 | 5/1988 | Heppke et al. | 252/299.61 |
| 4,765,924 | 8/1988 | Inoue et al. | 252/299.61 |
| 4,784,792 | 11/1988 | Inoue et al. | 252/299.61 |
| 4,798,680 | 1/1989 | Nohira et al. | 252/299.01 |
| 4,834,904 | 5/1989 | Krause et al. | 252/299.01 |
| 4,867,903 | 9/1989 | Nahira et al. | 252/299.61 |
| 4,892,393 | 1/1990 | Terashima et al. | 350/350 S |
| 4,904,410 | 2/1990 | Nahira et al. | 252/299.61 |

FOREIGN PATENT DOCUMENTS

| | | | |
|---|---|---|---|
| 255219 | 2/1988 | European Pat. Off. | |
| 3515373 | 11/1986 | Fed. Rep. of Germany | 252/299.61 |
| 62-228036 | 6/1987 | Japan | 252/299.66 |
| 63-22042 | 1/1988 | Japan | 252/299.61 |
| 63-51377 | 3/1988 | Japan | 252/299.61 |

Primary Examiner—Robert L. Stoll
Assistant Examiner—C. Harris
Attorney, Agent, or Firm—Wenderoth, Lind & Ponack

[57] ABSTRACT

A 2-substituted-alkyl ether having an optically active group and useful as a component of ferroelectric liquid crystal compositions and a liquid crystal composition containing the same are provided, which 2-substituted-alkyl ether is expressed by the formula $$R^1-(A)-(B)-O-CH_2-\overset{X}{\underset{*}{C}}H-R^2 \quad (I)$$

wherein $R^1$ represents a linear or branched chain alkyl, alkoxy, alkanoyl, alkanoyloxy or alkoxycarbonyl of 1 to 18 C; $R^2$ represents a linear or branched alkyl of 2 to 15 C;

$-(A)-$ and $-(B)-$ each independently represents

[ring structures: phenyl, cyclohexyl (H), pyridyl, pyrimidyl, pyrazinyl, pyridazinyl, and Y-substituted phenyl rings]

wherein Y represents cyano, halogen, methyl or methoxy; X represents $-OR^3$, $$-O\overset{O}{\underset{\|}{C}}R^3,$$

F, Cl or Br wherein $R^3$ represents a linear or branched alkyl group of 1 to 10 C of H; and * indicates asymmetric C.

9 Claims, No Drawings

2-SUBSTITUTED-ALKYL ETHER AND LIQUID CRYSTAL COMPOSITION

This application is a continuation of now abandoned application, Ser. No. 07/151,501 filed Feb. 2, 1988, abandoned.

BACKGROUND OF THE INVENTION

1. Field of the Invention

This invention relates to a novel organic compound and more particularly it relates to a 2-substituted-alkyl ether having an optically active group and being useful as a component of ferroelectric liquid crystal compositions.

2. Description of the Related Art

At present, TN (twisted nematic) type display mode has been most broadly employed. This TN liquid crystal display mode has many advantages such as low driving voltage, small power consumption, etc., but it is inferior in the aspect of the response rate to emissive type display elements such as cathode tube, electroluminescence, plasma display, etc. New TN type display elements having an increased twist angle up to 180°–270° have also been developed, but they are still inferior in the response rate. Efforts in various improvements have been made as described above, but a TN type display element having a high response rate has not yet been realized. However, a novel display mode using a ferroelectric liquid crystal which has recently been extensively researched has a possibility that the response rate is notably improved (Clarks et al, Applied Phys. lett., 36, 899 (1980)). This mode utilizes chiral smectic phases exhibiting ferroelectricity such as chiral smectic C phase (hereinafter abbreviated to SC*). Phases exhibiting ferroelectricity are not limited to SC* phase, but it has been known that phases of chiral smectic F, G, H, I, etc. also exhibit ferroelectricity.

Various characteristics are required for ferroelectric liquid crystal materials to be practically used for ferroelectric liquid crystal display elements, but at present there is no single compound which satisfies these characteristics; hence it is necessary to use ferroelectric liquid crystal compositions obtained by blending some liquid crystal compounds or non-liquid crystalline compounds.

Further, not only ferroelectric liquid crystal compositions consisting only of ferroelectric liquid crystal compounds are used, but also Japanese patent application laid-open No. Sho 60-36003 discloses that compounds or compositions exhibiting phases of achiral smectic C, F, G, H, I, etc. (hereinafter abbreviated to phases of SC, etc.) as basic substances can be blended with one or more kinds of compounds exhibiting ferroelectric liquid crystalline phases, whereby it is possible to make up the whole into a ferroelectric liquid crystal composition. Further, a report discloses that by blending compounds or compositions exhibiting phases of SC, etc. as basic substances with one or more kinds of compounds which are optically active but exhibit no ferroelectric liquid crystalline phase, it is possible to make up the whole into a ferroelectric liquid crystalline composition (Mol. Liq. Cryst., 89, 327 (1982)).

When these facts are summarized, it is seen that by blending one or more kinds of optically active compounds, irrespective of whether or not these compounds exhibit ferroelectric liquid crystalline phases, with basic substances, it is possible to constitute a ferroelectric liquid crystal composition. However, the optically active substances are preferred to exhibit liquid crystalline phases, and even when they exhibit no liquid crystalline phases, their structures are preferred to be similar to those of liquid crystal compounds, so to speak, quasi liquid crystalline substances.

SUMMARY OF THE INVENTION

The object of the present invention is to provide an optically active compound which is preferred as a component of ferroelectric liquid crystalline compositions as described above.

The present invention resides in a compound expressed by the formula

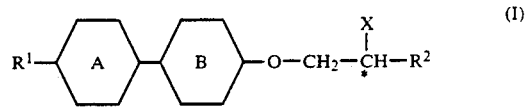

wherein $R^1$ represents a linear or branched chain alkyl group, alkoxy group, alkanoyl group, alkanoyloxy group or alkoxycarbonyl group, each of 1 to 18 carbon atoms; $R^2$ represents a linear or branched chain alkyl group, each of 2 to 15 carbon atoms;

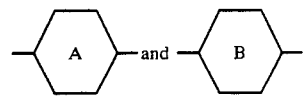

each independently represent

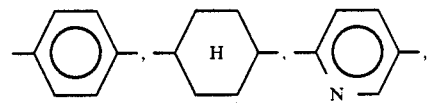

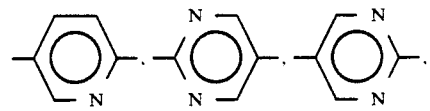

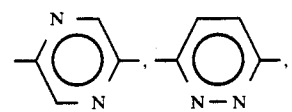

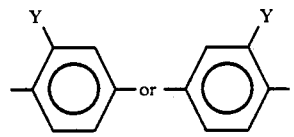

wherein Y represents cyano group, halogen atom, methyl group or methoxy group; and X represents $-OR^3$,

F, Cl or Br wherein $R^3$ represents a linear or branched chain alkyl group, each of 1 to 10 carbon atoms or hydrogen atom; and * indicates an asymmetric carbon atom, and a liquid crystal composition containing the same.

DETAILED DESCRIPTION OF PREFERRED EMBODIMENTS

In the formula (I), $R^1$ is preferably a linear chain alkyl group or alkoxy group, each of 4 to 14 carbon atoms and $R^2$ is preferably a linear or branched chain alkyl group of 2 to 10 carbon atoms, but in the case of the branched groups, they may have optical activity.

X is preferably F, —OCH$_3$ or

Preferably examples of

are as follows:

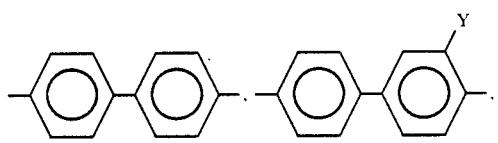

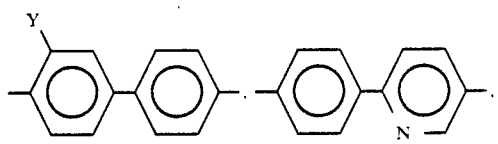

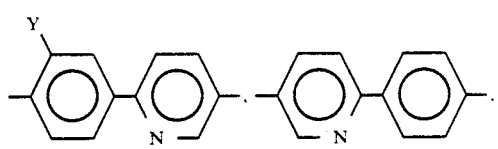

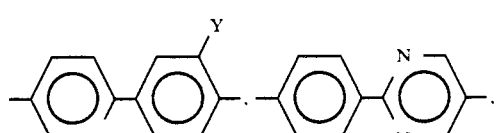

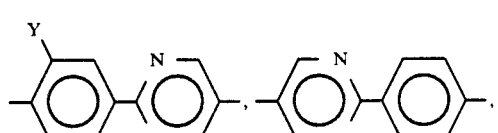

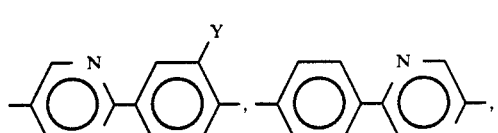

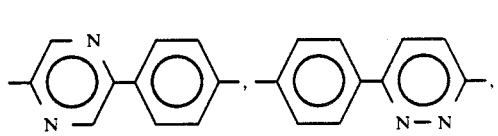

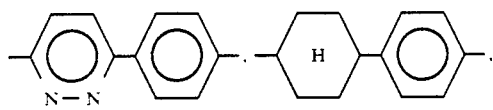

Y is the same as defined above and is preferably F, Cl, methyl or —CN.

The compound of the formula (I) may be prepared as follows.

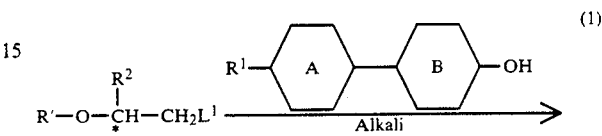

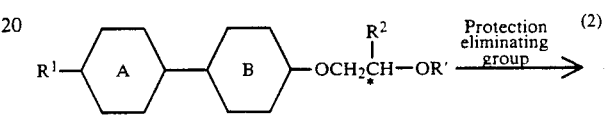

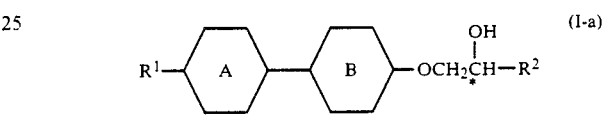

In the case of $X=OR^3$ (but $R^3 \neq H$),

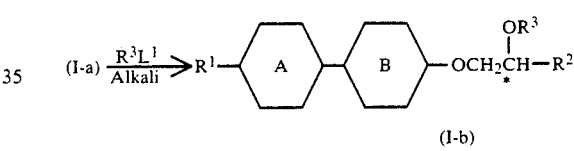

In the case of $$X = O\overset{O}{\underset{\|}{C}}R^3.$$

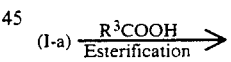

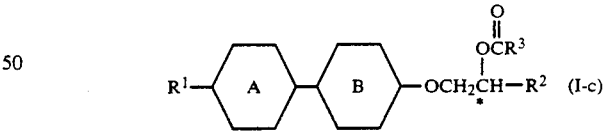

In the case of X = F, Cl or Br,

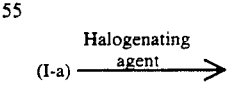

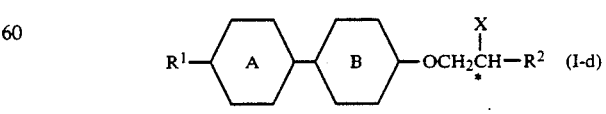

or

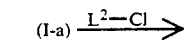

-continued

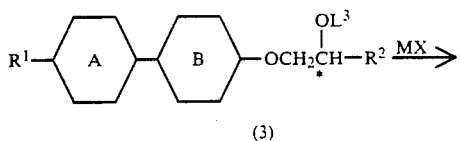

(3)

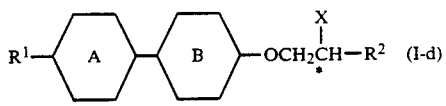

or only in the case of X=F,

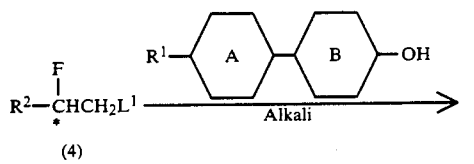

(4)

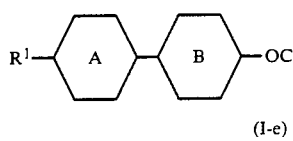

(1-e)

In the above equations, $R^1$, $R^2$, $R^3$,

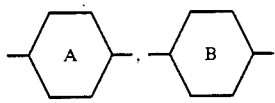

and X are as defined above; R' represents a protecting group such as 1-ethoxyethyl group, methoxymethyl group, 2-tetrahydropyranyl group, benzyl group, etc.; $L^1$ represents a group to be eliminated such as methanesulfonyloxy group, benzenesulfonyloxy group, p-toluenesulfonyloxy group, bromine, chlorine, etc.; $L^2$ represents methanesulfonyl group, benzenesulfonyl group, p-toluenesulfonyl group, etc.; and M represents a metal ion such as Li, Na, K, Ca, Ag, Hg, etc.

A compound (1) as a starting raw material is reacted with an alcohol or a phenol to obtain a compound (2), which is then subjected to protection-removal (herein denoted as "deprotection") in a manner suitable to a protecting group R' to obtain a compound (1-a). In this case, X in the formula (I) corresponds to $-OR^3$ wherein $R^3=H$. Further, by etherifying the compound of the formula (1-a) with $R^3L^1$, it is possible to prepare a compound of the formula (1-b). In this case, X corresponds to $-OR^3(R^3\ne H)$. Further, by esterifying a compound of the formula (1-a) with $R^3COOH$ or an active esterifying agent thereof, it is possible to prepare a compound of the formula (1-c). In this case, X corresponds to

Further, by treating the compound of the formula (1-a) for example with HF, hydrofluoric acid, HF-pyridine, $Et_2NCF_2CHClF$, $Et_2NSF_3$, fluorophenylphospho-ranes, etc., it is possible to prepare a compound wherein X=F in the compound of the formula (1-d).

Further, by treating the compound of the formula (1-a) with for example hydrogen chloride, thionyl chloride, phosphorus pentachloride, phosphorus oxychloride, triphenylphosphine and CCl6hd 4, etc., it is possible to prepare a compound of the formula (1-d) wherein X=Cl. Further, by treating the compound of the formula (1-a) with for example, hydrogen bromide, thionyl bromide, phosphorus tribromide, trialkylphosphine and $CCl_4$, etc., it is possible to prepare a compound of the formula (1-d) wherein X=Br.

Furthermore, by sulfonylating the compound of the formula (1-a) with methanesulfonyl chloride, p-toluenesulfonyl chloride, benzenesulfonyl chloride, etc., the compound is converted into a compound (3), which is then subjected to exchange reaction with fluorine atom using a salt such as LiF, KF, $CaF_2$, AgF, etc. to prepare a compound wherein X of the compound (1-d) is F. Further, by subjecting the compound (3) to exchange reaction with chlorine atom using a salt such as LiCl, $MgCl_2$, NaCl, etc., it is possible to prepare a compound (1-d) wherein X is Cl. Further, by subjecting the compound (3) to exchange reaction with bromine atom using a salt such as NaBr, KBr, etc., it is possible to prepare a compound wherein X of the compound (1-d) is Br.

Further, only in the case of X=F, is it possible to prepare a compound (1-e), using a compound (4) as raw material.

Here, preparations of the compounds (1) and (4) to be used as raw material will be described. The compound (1) may be prepared using as a raw material, an optically active α-hydroxyalkanoic acid, which may be prepared by chemical optical resolution of a racemic α-hydroxyalkanoic acid following by biochemical asymmetric esterification and asymmetric reduction, substitution of amino group of an amino acid into hydroxyl group according to Van Slyke's reaction, etc. Further, the compound (1) may be prepared by halogenating only 1-position of an optically active 1,2-alkanediol and using the resulting a 1-halo-2-hydroxyalkane as raw material, and the 1,2-alkanediol may be prepared using an optically active 1,2-epoxyalkane as raw material. The compound (4) may be prepared by using as raw material, an α-fluorinated alkanoic acid obtained by conversion of an amino group of an amino acid into fluorine, or a 2-fluorinated-alkan-1-ol obtained by fluorinating a 1,2-epoxyalkane in an acidic state.

Examples of the above amino acid are 2-aminobutanoic acid, valine, leucine, isoleucin, norvaline, norleucine, etc.

Besides the preparations illustrated above, it is also possible to prepare the compound of the formula (I) of the present invention by combining known methods.

As to one of the specific features of the compound of the formula (I) of the present invention, those which exhibit ferroelectric liquid crystalline phases by themselves are naturally suitable as a component of ferroelectric liquid crystal compositions (for example, Example 24 described later), but even those which exhibit no ferroelectric liquid crystalline phase by themselves are also suitable as a component of ferroelectric liquid crystal compositions (for example, Examples 25 and 26 mentioned later). Further, when the above compound is added in a suitable quantity to achiral or chiral smectic liquid crystal compounds (and/or compositions), the spontaneous polarization value of the resulting ferroelectric liquid crystal compositions notably increases as compared with that prior to the addition. Namely, since liquid crystal compounds or compositions exhibiting phases of achiral smectic C, etc. are not ferroelectric liquid crystal, Ps is absent, but when the compound of the present invention is added to the substances, the resulting compositions exhibit ferroelectric liquid crystalline phases, and Ps notably increases depending on the addition quantity. Further, when the compound of the present invention is added in a suitable quantity to ferroelectric liquid crystal compounds (and/or compositions) having a slightest Ps value, it is possible to notably increase the Ps value and also to shorten the response time as compared with that prior to the addition. Namely, the compound of the present invention is preferred as a component for adjusting to Ps value of ferroelectric liquid crystal compositions.

Further, as illustrated in Example 27 mentioned later, since the compound of the formula (I) of the present invention has an optically active carbon atom, it has a capability of inducing a twisted structure by adding it to nematic liquid crystals. Since nematic liquid crystals having a twisted structure, i.e. chiral smectic liquid crystals, form no reverse twist domain of TN type display elements, the compound of the formula (I) of the present invention also has a function as an agent for preventing the reverse twist domain from forming.

Further, many of chiral nematic liquid crystal compositions obtained by adding the compound of the present invention to nematic liquid crystal compositions have very flat temperature characteristics of chiral pitch, as illustrated in Example 28 mentioned later. Most of chiral substances currently used for addition to nematic liquid crystals have a chiral pitch which becomes longer with temperature rise. However, those having a chiral pitch which becomes shorter with temperature rise have also been reported and also it has been stated therein that such substances reduce the temperature change in the threshold voltage as electro-optical characteristics of TN type display elements (see 33rd Associated Lecture Meeting Related to Applied Physics (Preprints 1p-G-7 (p. 78), Spring, 1986) and Japan Display 86, Preprints 8.3 (p. 286-289)).

Since the compound of the present invention has physical properties similar to the above, it is possible to reduce the temperature change in the threshold voltage of chiral nematic liquid crystal compositions obtained by adding it.

Further, apart therefrom, in the case of the so-called super TN type display having the twist angle changed to 180°-270°, the temperature change in the pitch notably reduces the display grade, but when a chiral nematic liquid crystal composition is obtained by adding the compound of the present invention to the super TN type display compositions, it is possible to prepare an excellent super TN type display element whose display grade is not damaged by the temperature change.

As described above, the compound of the present invention is also useful as a chiral component compound of chiral nematic compositions.

The compound and liquid crystal composition of the present invention will be described in more detail by way of Examples.

EXAMPLE 1

Preparation of S-1-(4'-octyloxy-4-biphenyloxy)-4-methyl-pentane-2-ol (a compound of the formula (I) wherein $R^1$ represents octyloxy,

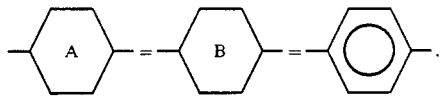

$R^2$ represents isobutyl and X represents OH)

(1) Preparation of 2S-2-(2'-tetrapyranyloxy)-4-methyl-pentane-1-ol

A suspension of S-leucine (100 g) in 2N-sulfuric acid (1,600 ml) was cooled down to 0° to 5° C., followed by gradually adding solid sodium nitrite (90 g). After the mixture became a transparent solution, this solution was allowed to stand at room temperature overnight, followed by distilling off water under reduced pressure, adding ethyl acetate (500 ml) to the resulting residue to remove the resulting solids, drying the mother liquor with $MgSO_4$, concentrating it, adding ethanol (160 ml), benzene (300 ml), and p-toluenesulfonic acid hydrate (2 g), heating the mixture under reflux for 12 hours while removing the resulting water, washing the resulting material with water and distilling under reduced pressure to obtain ethyl 2S-2-hydroxy-4-methylpentanoate (b.p. 52°-54° C./3 mmHg, $\alpha_D^{25}$-12.0 (neat)) (25 g). A mixture of this product (17 g), 3,4-dihydropyran (14 g) and dichloromethane (100 ml) was cooled down to 0° C., followed by dropwise adding a solution of pyridium-p-toluenesulfonate (1.0 g) in dichloromethane (30 ml), agitating the mixture at 0° C. for 2 hours, further agitating it at room temperature for 10 hours, again cooling the resulting material, adding solid sodium hydrogen carbonate (1.0 g), concentrating the resulting solution, subjecting the concentrate to column chromatography using a column having silica gel filled therein and using heptane as an eluent, concentrating the resulting elute, and distilling the concentrate under reduced pressure to obtain ethyl 2S-2-(2'-tetrahydropyranyloxy)-4-methylpentanoate (b.p. 85°-103° C./4 mmHg, $\alpha_D^{25}$-42.2 (neat)) (20 g). Lithium aluminum hydride (2.4 g) was suspended in tetrahydrofuran (hereinafter abbreviated to THF) (50 ml) and the suspension was cooled. To this suspention was dropwise added a solution of the above ethyl 2S-2-(2'-tetrahydropyranyloxy)-4-methyl-pentanoate (20 g) in THF (200 ml), followed by adding water after completion of the reaction, extracting the mixture with ether and distilling the resulting material under reduced pressure to obtain 2S-2-(2'-tetrahydropyranyloxy)-4-methyl-pentan-1-ol (b.p. 90°-105° C./3 mmHg, $\alpha_D^{24}$-29.0 (neat)) (15 g).

(2) Preparation of 2S-2-(2'-tetrahydropyranyloxy)-4-methyl-pentyl-p-toluenesulfonate 2S-2-(2'-tetrahydropyranyloxy)-4-methyl-pentane-1-ol obtained in the above item (1) (15 g) was dissolved in pyridine (100 ml) and the solution was cooled. To this solution was dropwise added a solution of p-toluenesulfonyl chloride (15 g) in pyridine (200 ml), followed by adding toluene (300 ml) for extraction, washing the resulting organic layer with water, then with an alkali and further with water, drying and concentrating it to obtain 2S-2-(2'-tetrahydropyranyloxy)-4-methyl-pentyl-p-toluenesulfonate (30 g).

(3) Preparation of S-1-(4'-octyloxy-4-biphenyloxy)-4-methyl-pentan-2-ol

THF (20 ml) was added to sodium hydride (55%) (1.7 g) and the solution was cooled, followed by adding to the solution, a solution of 4'-hydroxy-4-octyloxy-biphenyl (8 g) in THF (100 ml), successively adding a solution of 2S-2-(2'-tetrahydropyranyloxy)-4-methyl-pentyl-p-toluenesulfonate (10 g) obtained above in the item 2 in N,N-dimethylformamide (hereinafter abbreviated to DMF) (200 ml), heating the mixture at 80°-90° C. for 8 hours, cooling the resulting material, adding toluene (300 ml), washing with water, then with an alkali and further with water, concentrating, purifying the concentrate according to column chromatography using a column having activated alumina filled therein and using toluene as an eluent, concentrating the resulting elute, adding ethanol (300 ml), further adding 12M+HCl (5 ml), heating the mixture at 60° C. for 2 hours, cooling, filtering off the resulting solids, and recrystallizing from a mixed solution of ethanol with ethyl acetate to obtain S -1-(4'-octyloxy-4-biphenylyloxy)-4-methylpentan-2-ol ([α]$_D^{24}$+8.2 (C 0.54, CHCl$_3$)) (8 g). This product exhibited phase transition points of C 95° C. (S$_5$.58° C.), S$_4$.103° C., S$_3$.113.1° C., S$_2$.113.6° C., S$_1$.115.6° C., SA.119.5° C. and I wherein C represents crystalline phase; I , isotropic liquid phase; SA, smectic A phase; S$_1$-S$_5$, smectic phases whose attributions are at present unknown; and ( ), monotropic phase.

EXAMPLE 2

Preparation of S-1-(4(5-decyl-2-pyridinyl)-phenoxy)-4-methyl-pentane-2-ol (a compound of the formula (I) wherein R$^1$ represents decyl,

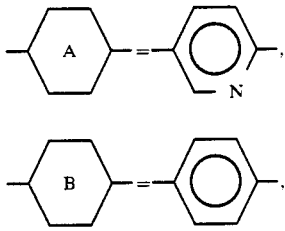

R$^2$ represents isobutyl and X represents OH)

Using sodium hydride (2.0 g), p-(5-decyl-2-pyridinyl)-phenol (m.p. 90.4°-91.8° C.) (9 g) and 2S-2-(2'-tetrahydropyranyloxy)-4-methyl-pentyl-p-toluenesulfonate (10 g) obtained in Example 1-(2), and in the same manner as in Example 1-(3), the objective compound, S-1-(4-(5-decyl-2-pyridinyl)-phenoxy)-4-methyl-pentane-2-ol ([α]$_D^{24}$6.4 (C0.5CHCl$_3$)) (8.5 g) was obtained. In addition, the above-mentioned p-(5-decyl-2-pyridinyl)-phenol is obtained according to the process disclosed in Japanese patent application No. Sho 60-293934/1985 wherein p-methoxyphenyl-β-chlorovinyl ketone and N-dodecenylpiperidine as known substances are reacted together, followed by reacting the reaction product with perchloric acid to obtain pyrylium perchlorate, reacting this compound with ammonium acetate to obtain 5-decyl-2-(p-methoxyphenyl)-pyridine, and further reacting this compound with aqueous hydrogen bromide in acetic acid for demethylation.

The captioned compound has a m.p. of 108.3°-109.2° C. and its proton NMR was as follows:

| (CDCl$_3$ solution, TMS internal standard) | | |
|---|---|---|
| δ (ppm) | | |
| 8.42 | s | 1 H |
| 7.85 | d (J = 9 Hz) | 2 H |
| 7.48 | s | 2 H |
| 6.90 | d (J = 9 Hz) | 2 H |
| 4.23 ~ 3.73 | m | 3 H |
| 3.25 | s | 1 H |
| 2.58 | t (J = 7 Hz) | 2 H |
| 2.17 ~ 0.75 | m | 28 H |

EXAMPLE 3

Preparation of S-1-(4-(5-octyl-2-pyrimidinyl)-phenoxy)-4-methyl-pentane-2-ol (a compound of the formula (I) wherein R$^1$ represents octyl,

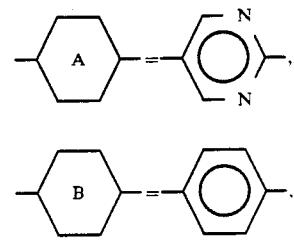

R$^2$ represents isobutyl and X represents OH)

Using sodium hydride (1.5 g) p-(5-octyl-2-pyrimidinyl)-phenol (6 g) and 2S-2-(2'-tetrahydropyranyloxy)-4-methyl-pentyl-p-toluenesulfonate obtained in Example 1-(2) (10 g) and in the same manner as in Example 1-(3), the captioned compound i.e. S-1-(4-(5-octyl-2-pyrimidinyl)-phenoxy)-4-methyl-pentane-2-ol ([α]$_D^{24}$8.6 (C 0.53, CHCl$_3$)) (5 g) was obtained. This product exhibited a m.p. of 93.7°-94.2° C.

EXAMPLE 4

Preparation of S-4'-octyloxy-4-(4-methyl-2-methoxy-pentoxy)-biphenyl (a compound of the formula (I) wherein R$^1$ represents octyloxy,

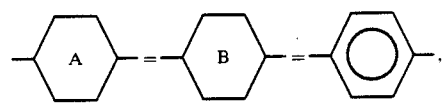

R$^2$ represents isobutyl and X represents —OCH$_3$)

Sodium hydride (55%) (0.2 g) was suspended in THF and the resulting suspension was cooled, followed by adding thereto a solution of S-1-(4'-octyloxy-4-biphenylyloxy)-4-methyl-pentane-2-ol obtained in Example 1-(3) (1.0 g) in DMF (50 ml), further adding a solution of methyl iodide (1.0 g) in DMF (30 ml), agitating the mixture at 60°-70° C. for 8 hours, adding thereto toluene (100 ml), washing with water, then with an alkali, further with an acid and furthermore with water, thereafter concentrating, purifying the residue according to column chromatography using a column having activated alumina filled therein, concentrating the resulting elute and twice recrystallizing from ethanol (50 ml) to obtain the captioned compound, S-4'-octyloxy-4-(4-methyl-2-methoxy-pentoxy)-biphenyl (0.7 g). This product exhibited a m.p. of 61.8°-62.8° C. Its specific rotatory power was [α]$_D^{22}$−21.2 (C 0.47, CHCl$_3$).

EXAMPLE 5

Preparation of S-4'-octyloxy-4-(4-methyl-2-acetyloxy)-pentoxy biphenyl (a compound of the formula (I) wherein $R^1$ represents octyloxy,

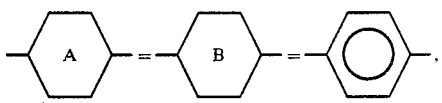

$R^2$ represents isobutyl and X represents

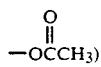

A mixture of S-1-(4'-octyloxy-4-biphenylyloxy)-4-methyl-pentane-2-ol (1.0 g) obtained in Example 1-(3), 4N,N-dimethylaminopyridine (hereinafter abbreviated to DMAP) (50 mg) and acetic anhydride (40 ml) was heated on a water bath at 60° C. for 4 hours, followed by adding toluene (100 ml), washing the organic layer with an alkali, then with an acid and further with water, concentrating, purifying it according to column chromatography using a column having activated alumina filled therein and using toluene as eluent, concentrating the elute and twice recrystallizing the residue from ethanol (40 ml) to obtain the captioned compound, S-4'-octyloxy-4-(4-methyl-2-acetyloxy)-pentoxy-biphenyl (0.8 g). This product exhibited a m.p. of 53.7°–54.7° C. Its specific rotatory power was $[\alpha_D^{21}] - 39.2$ (C 0.51, CHCl$_3$).

EXAMPLE 6

Preparation of S-5-decyl-2-(4-(4-methyl-2-acetyloxy)-pentoxy-phenyl)-pyridine (a compound of the formula (I) wherein $R^1$ represents decyl,

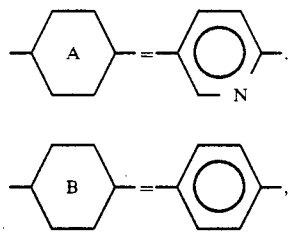

$R^2$ represents isobutyl and X represents

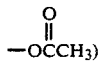

Reaction and purification were carried out in the same manner as in Example 5, using S -1-(4-(5-decyl-2-pyridinyl)-phenoxy)-4-methyl-pentane-2-ol (1.0 g) obtained in Example 2, DMAP (50 mg) and acetic anhydride (40 ml), to obtain the captioned compound, S-5-decyl-2-(4-(4-methyl-2-acetyloxy)-pentoxy-phenyl)-pyridine (0.5 g). This product had a m.p. of 39.3°–41.0° C. and its specific rotatory power was $[\alpha]^{27}_D - 35.3$ (C 0.53, CHCl$_3$).

Further, its proton NMR was as follows:

| (CDCl$_3$ solution, TMS internal standard) | | |
|---|---|---|
| δ (ppm) | | |
| 8.47 | s | 1 H |
| 7.90 | d (J = 9 Hz) | 2 H |
| 7.50 | s | 2 H |
| 6.97 | d (J = 9 Hz) | 2 H |
| 5.53 ~ 5.13 | m | 1 H |
| 4.02 | d (J = 5 Hz) | 2 H |
| 2.60 | t (J = 7 Hz) | 2 H |
| 2.03 | s | 3 H |
| 1.83 ~ 0.80 | m | 28 H |

EXAMPLE 7

Preparation of S-5-octyl-2-(4-(4-methyl-2-acetyloxy)-pentoxy-phenyl)-pyrimidine (a compound of the formula (I) wherein $R^1$ represents octyl,

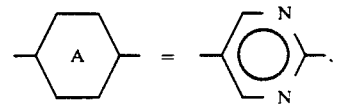

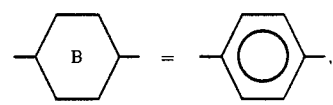

$R^2$ represents isobutyl and X represents

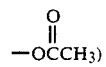

Reaction and purification were carried out in the same manner as in Example 5, using S-1-(4-(5-octyl-2-pyrimidinyl)-phenoxy)-4-methyl-pentane-2-ol (0.8 g) obtained in Example 3, DMAP (30 mg) and acetic anhydride (20 ml), to obtain the captioned compound, S-5-octyl-2-(4-(4-methyl-2-acetyloxy)-pentoxy-phenyl)-pyrimidine (0.3 g). This product had a m.p. of 41.3°–41.5° C.

EXAMPLE 8

Preparation of 5-decyl-2-(4-(4-methyl-2-chloro)-pentoxy-phenyl)-pyridine (a compound of the formula (I) wherein $R^1$ represents decyl,

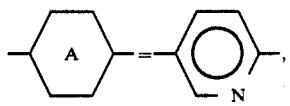

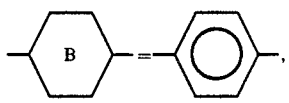

$R^2$ represents isobutyl and X represents Cl)

A mixture of S-1-(4-(5-decyl-2-pyridinyl)-phenoxy)-4-methyl-pentane-2-ol (1.0 g) obtained in Example 2, triphenylphosphine (hereinafter abbreviated to TPP) (1.2 g), CCl$_4$ (20 ml) and CH$_2$Cl$_2$ (40 ml) was agitated at room temperature for 20 hours, followed by washing with an acid, then with an alkali and further with water, purifying according to column chromatography using a column having activated column filled therein and recrystallizing from ethanol, to obtain the captioned compound, 5-decyl-2-(4-(4-methyl-2-chloro)pentoxyphenyl)-pyridine (0.6 g). Its m.p. was 61.4°–63.1° C. and its specific rotatory power was $[\alpha]_D^{22}+11.9$ (C 0.9, CHCl$_3$). Further, its proton NMR was as follows:

| (CDCl$_3$ solution, TMS internal standard) | | |
|---|---|---|
| δ (ppm) | | |
| 8.43 | s | 1 H |
| 7.90 | d (J = 9 Hz) | 2 H |
| 7.52 | s | 2 H |
| 6.98 | d (J = 9 Hz) | 2 H |
| 4.43 ~ 3.83 | m | 3 H |
| 2.62 | t (J = 7 Hz) | 2 H |
| 2.17 ~ 0.67 | m | 28 H |

EXAMPLE 9

Preparation of 5-octyl-2-(4-(4-methyl-2-chloro)pentoxy-phenyl)-pyrimidine (a compound of the formula (I) wherein R$^1$ represents octyl,

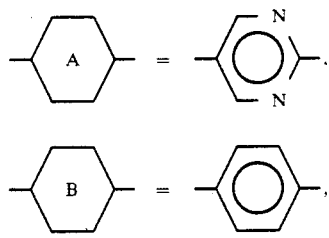

R$^2$ represents isobutyl and X represents Cl)

Reaction and purification were carried out in the same manner as in Example 8, using S-1-(4-(5-octyl-2-pyrimidinyl)-phenoxy)-4-methyl-pentane-2-ol (0.8 g) obtained in Example 3, TPP (1.2 g), CCl$_4$ (10 ml) and CH$_2$Cl$_2$ (30 ml), to obtain the captioned compound, 5-octyl-2-(4-(4-methyl-2-chloro)-pentoxy-phenyl)-pyrimidine (0.4 g). Its m.p. was 79.5°–80.0° C.

EXAMPLE 10

Preparation of 5-decyl-2-(4-(4-methyl-2-fluoro)pentoxy-phenyl)-pyridine (a compound of the formula (I) wherein R$^1$ represents decyl,

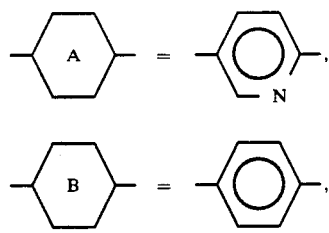

R$^2$ represents isobutyl and X represents F)

A solution of (Et)$_2$NSF$_3$ (diethylaminosulfate fluoride; hereinafter abbreviated to DAST) (0.4 g) in CH$_2$Cl$_2$ (30 ml) was cooled down to −50° C., followed by dropwise adding to the solution, a solution of S-1-(4-(5-decyl-2-pyridinyl)-phenoxy)-4-methyl-pentane-2-ol (1.0 g) obtained in Example 2 in CH$_2$Cl$_2$ (50 ml), slowly returning the temperature to room temperature, washing the reaction liquid with an acid, then with an alkali and further with water, concentrating it, purifying the residue according to column chromatography using a column having activated alumina filled therein and recrystallizing from ethanol (40 ml), to obtain the captioned compound, 5-decyl-2-(4-(4-methyl-2-fluoro)-pentoxy-phenyl)-pyridine (0.4 g). Its m.p. was 77.0°–78.0° C. Further, its specific rotatory power was $[\alpha]_D^{25}4.3$ (C 0.5, CHCl$_3$).

EXAMPLE 11

Preparation of S-5-(2'-fluorooctyloxy)-2-(4'-octyloxyphenyl)pyrimidine (a compound of the formula wherein R$^1$ represents octyloxy,

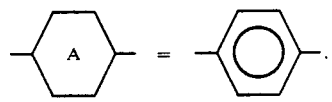

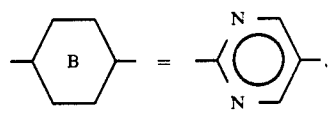

R$^2$ represents hexyl and X represents F)

(1) Preparation of S-2-fluoro-octane-1-ol

A solution HF-pyridine solution (30 ml) was cooled with ice, followed by dropwise adding a solution of R-1,2-epoxyoctane (8.5 g) in ether (20 ml), agitating the mixture at the same temperature for 2 hours, returning the temperature to room temperature, adding water (100 ml), twice extracting with ether (50 ml), washing the organic layer with an alkali and then with water, drying over MgSO$_4$, concentrating, distilling the concentrate under reduced pressure to obtain a fraction of 126°–129° C./80 mmHg (4.9 g), and recrystallizing it from heptane (40 ml) to obtain S-2-fluoro-octane-1-ol (3.7 g) $[\alpha]_D^{26}-13.14$ (C 1.7, C$_6$H$_6$) m.p. 33°–35° C.

(2) Preparation of S-2-fluoro-1-p-toluenesulfonyloxyoctane

S-2-fluoro-octane-1-ol (3.0 g) obtained in the above (1), p-toluenesulfonyl chloride (1.5 g) and pyridine (50 ml) were agitated at room temperature, followed by adding water (100 ml) and toluene (200 ml), separating the organic layer, washing it with an acid, then with an alkali and further with water, drying over MgSO$_4$ and concentrating to obtain S-2-fluoro-1-p-toluenesulfonyloxyoctane (6.0 g).

(3) Preparation of S-5-(2'-fluorooctyloxy)-2-(4-octyloxyphenyl)pyrimidine

THF (10 ml) was added to sodium hydride (80 mg), followed by adding 5-hydroxy-2-(4'-octyloxyphenyl)-pyrimidine (300 mg), further adding S-2-fluoro-1-p-toluenesulfonyloxyoctane (300 mg) obtained in the above (2), adding DMF (50 ml), agitating the mixture at a temperature in the vicinity of 70° C. for 8 hours, adding toluene (150 ml), separating the organic layer, washing it with an alkali and then with water, concentrating, purifying according to column chromatography using a column having activated alumina filled therein and using toluene as an eluent and recrystallizing from ethanol to obtain the captioned S-4-(2'-fluorooctyloxy)-2-(4'-octyloxyphenyl)pyrimidine (150 mg).

This product exhibited phase transition points of

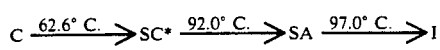

EXAMPLE 12

Using 5-hydroxy-2-(4'-nonylphenyl)pyrimidine in place of 5-hydroxy-2-(4'-octyloxyphenyl)pyrimidine in Example 11-(3), there was obtained S-5-(2'-fluorooctyloxy)-2-(4'-nonylphenyl)pyrimidine (a compound of the formula (I) wherein $R^1$ represents nonyl,

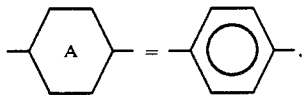

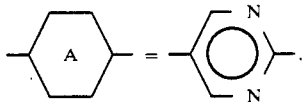

$R^2$ represents hexyl and X represents F).

This product exhibited phase transition points of

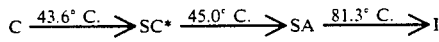

EXAMPLE 13

Using 5-octyl-2-(4'-hydroxyphenyl)pyrimidine in place of 5-hydroxy-2-(4'-octyloxyphenyl)pyrimidine in Example 11-(3), there was obtained S-5-octyl-2-(4'-(2''-fluorooctyloxy)phenyl)pyrimidine (a compound of the formula (I) wherein $R^1$ represents octyl,

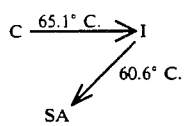

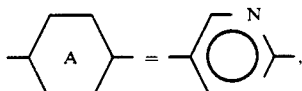

$R^2$ represents hexyl and X represents F).

This product exhibited phase transition points of $$C \xrightarrow{65.1°\,C.} I$$
$$\searrow \quad 60.6°\,C.$$
$$SA$$

EXAMPLE 14

Using 5-heptyl-2-(3'-fluoro-4'-hydroxyphenyl)pyrimidine in place of 5-hydroxy-2-(4'-octyloxyphenyl)pyrimidine in Example 11-(3), there was obtained S-5-heptyl-2-(3'-fluoro-4'-(2''-fluorooctyloxy)phenyl)pyrimidine (a compound of the formula (I) wherein $R^1$ represents heptyl,

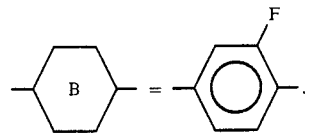

-continued

$R^2$ represents hexyl and X represents F).

This product exhibited phase transition points of $$C \xrightarrow{41.2°\,C.} SA \xrightarrow{41.6°\,C.} I$$

EXAMPLE 15

Using 4'-hydroxy-4-octyloxybiphenyl in place of 5-hydroxy-2-(4'-octyloxyphenyl)pyrimidine in Example 11-(3), there was obtained S-4'-octyloxy-4-(2'-fluorooctyloxy)biphenyl (a compound of the formula (I) wherein $R^1$ represents octyloxy,

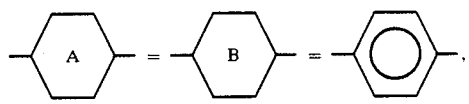

$R^2$ represents hexyl and X represents F).

This product exhibited a m.p. of 113.0° C.

EXAMPLE 16

Using 4'-hydroxy-4-octylbiphenyl in place of 5-hydroxy-2-(4'-octyloxyphenyl)pyrimidine in Example 11-(3), there was obtained S-4'-octyl-4-(2'-fluorooctyloxy)biphenyl (a compound of the formula (I) wherein $R^1$ represents octyl,

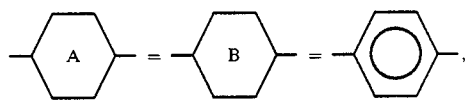

$R^2$ represents hexyl and X represents F).

This product exhibited a m.p. of 92.4° C.

EXAMPLE 17

Using 3'-fluoro-4'-hydroxy-4-dodecylbiphenyl in place of 5-hydroxy-2-(4'-octyloxyphenyl)pyrimidine in Example 11-(3), there was obtained S-4'-dodecyl-3-fluoro-4-(2'-fluorooctyloxy)biphenyl (a compound of the formula (I) wherein $R^1$ represents dodecyl,

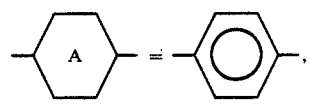

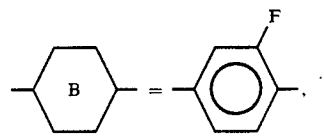

$R^2$ represents hexyl and X represents F).

This product exhibited a m.p. of 73.8° C.

EXAMPLE 18

Using 3'-chloro-4'-hydroxy-4-dodecylbiphenyl in place of 5-hydroxy-2-(4'-octyloxyphenyl)pyrimidine in Example 11-(3), there was obtained S-4'-dodecyl-3-chloro-4-(2'-fluorooctyloxy)biphenyl (a compound of the formula (I) wherein $R^1$ represents dodecyl,

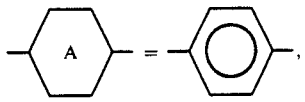

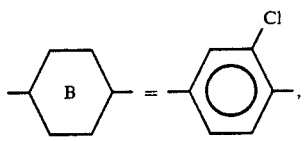

$R^2$ represents hexyl and X represents F).
This product exhibited a m.p. of 49.9° C.

EXAMPLE 19

Using 5-decyl-2-(4'-hydroxyphenyl)pyridine in place of 5-hydroxy-2-(4'-octyloxyphenyl)pyrimidine in Example 11-(3), there was obtained S-5-decyl-2-(4'-(2''-fluorooctyloxy)phenyl)pyridine (a compound of the formula (I) wherein $R^1$ represents decyl,

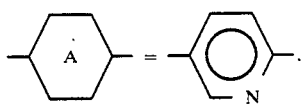

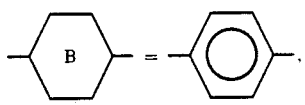

$R^2$ represents hexy and X represents F).
This products exhibited phase transition points of

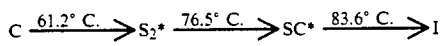

($S_2^*$ is a ferroelectric smectic phase whose attribution is unknown).

EXAMPLE 20

Using 5-octyl-2-(4'-hydroxyphenyl)pyridine in place of 5-hydroxy-2-(4'-octyloxyphenyl)pyrimidine in Example 11-(3), there was obtained S -5-octyl-2-(4'-(2''-fluorooctyloxy)phenyl)pyridine (a compound of the formula (I) wherein $R^1$ represents octyl,

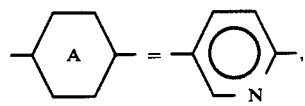

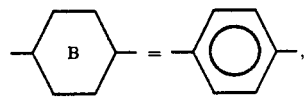

$R^2$ represents hexyl and X represents F).
This compound exhibited phase transition points of

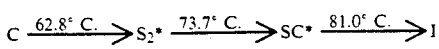

EXAMPLE 21

Using 5-heptyl-2-(3'-fluoro-4'-hydroxyphenyl)pyridine in place of 5-hydroxy-2-(4'-octyloxyphenyl)pyrimidine in Example 11-(3), there was obtained 5-heptyl-2-(3'-fluoro-4'-(2''-fluorooctyloxy)phenyl)pyridine (a compound of the formula (I) wherein $R^1$ represents heptyl,

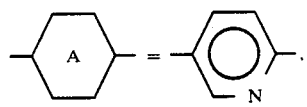

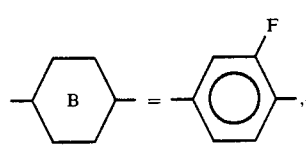

$R^2$ represents hexyl and X represents F).
This product exhibited phase transition points of

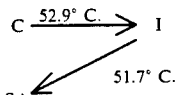

EXAMPLE 22

Using 4-(4'-pentyl-trans-cyclohexyl)phenol in place of 5-hydroxy-2-(4'-octyloxyphenyl)pyrimidine in Example 11-(3), there was obtained 1-(2'-fluorooctyloxy)-4-(4''-pentyl-trans-cyclohexyl)benzene (a compound of the formula (I) wherein $R^1$ represents pentyl,

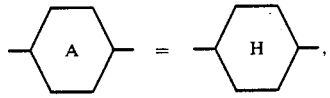

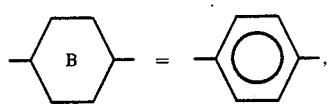

$R^2$ represents hexyl and X represents F).
This product exhibited phase transition points of

EXAMPLE 23

A mixture of sodium hydride (80 mg), S-2-fluorooctane-1-ol (200 mg) obtained in Example 11-(1), 3-chloro-6-(4'-heptyloxyphenyl)pyridazine (400 mg) and toluene (50 ml) was heated under reflux for 6 hours, followed by adding water (100 ml), washing with an alkali and then with water, concentrating, purifying according to column chromatography using a column having activated alumina filled therein and recrystallizing from ethanol to obtain 3-(2'-fluorooctyloxy)-6-(4-heptyloxyphenyl)-pyridazine (a compound of the formula (I) wherein R¹ represents heptyloxy,

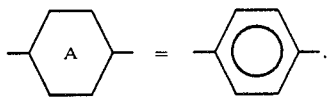

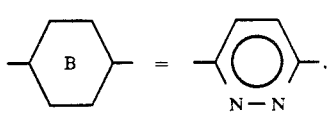

| Temperature (°C.) | Response time (μ sec) | Ps(nC/cm²) |
|---|---|---|
| 82 | 22 | 94.4 |
| 72 | 30 | 146.3 |
| 62 | 65 | 192.1 |

As seen from the above, compounds which singly exhibit ferroelectricity can constitute a display element having a high response rate.

EXAMPLE 25

Use example 2

A liquid crystal composition (A) consisting of

CH₃(CH₂)₅—O—〈phenyl〉—〈pyridazine N-N〉—(CH₂)₇CH₃  30 wt. %

CH₃(CH₂)₇—O—〈phenyl〉—〈pyridazine N-N〉—(CH₂)₇CH₃  20 wt. %

CH₃(CH₂)₈—O—〈phenyl〉—〈pyridazine N-N〉—(CH₂)₇CH₃  10 wt. %

CH₃(CH₂)₉—O—〈phenyl〉—〈pyridazine N-N〉—(CH₂)₇CH₃  10 wt. %

CH₃(CH₂)₄—O—〈phenyl〉—〈phenyl〉—〈pyridazine N-N〉—(CH₂)₇—CH₃  20 wt. %

CH₃(CH₂)₆—O—〈phenyl〉—〈phenyl〉—〈pyridazine N-N〉—(CH₂)₇—CH₃  10 wt. %

R² represents hexyl and X represents F). (200 mg).

EXAMPLE 24

(Use example 1)

S-5-(2'-fluorooctyloxy)-2-(4'-octyloxyphenyl)pyridine obtained in Example 11 was filled in a cell of 2 μ thickness provided with transparent electrodes each obtained by coating PVA as an aligning agent onto the surface and rubbing the resulting surface to subject it to a parallel aligning treatment, followed by placing the resulting element between two sheets of crossed polarizers and impressing an electric field. The response time was sought from the change in the intensity of transmitted light by impressing ±10V and Ps (spontaneous polarization value) was sought according to Sowyer-Tower method. The results were as follows:

exhibits phase transition points of C →SC 4° C., SC →SA 65° C., SA →N 79° C., Ne →I 90° C. (SC is an abbreviation of smectic C phase and N is that of nematic phase). Further, since this composition (A) consists only of non-optically active compounds, it is not a chiral liquid crystal and hence is not a ferroelectric liquid crystal and exhibits no spontaneous polarization. A mixture (a composition (B)) of the composition (A) (20% by weight) with the compound of Example 5 of the present invention (20% by weight) was unclear in Cr→SC*, but exhibited phase transition points of SC* →SA 50° C., SA →N* 72.2° C. and N* →I 81.6° C. (N* is an abbreviation of chiral nematic phase). With this composition (B), the response time and Ps were sought in the same manner as in Example 24. The results were as follows:

| Temperature (°C.) | Response time (μ sec) | Ps (nC/cm²) |
|---|---|---|
| 45 | 75 | 1.8 |

-continued

| Temperature (°C.) | Response time (μ sec) | Ps (nC/cm²) |
| --- | --- | --- |
| 35 | 125 | 3.0 |
| 25 | 180 | 3.5 |

EXAMPLE 26

Use example 3

A mixture (a composition (C)) of the composition (A) in Example 25 (80% by weight) with the compound of Example 10 of the present invention (20% by weight) was unclear in C→SC*, but exhibited phase transition points of SC*→SA 58.0° C. and SA→I 82.0° C. With this composition (C), the response time and Ps were sought under the conditions as in Example 24. The results were as follows:

| Temperature (°C.) | Response time (μ sec) | Ps (nC/cm²) |
| --- | --- | --- |
| 50 | 30 | 6.0 |
| 40 | 48 | 8.0 |
| 30 | 65 | 8.8 |
| 20 | 76 | 9.0 |

EXAMPLE 27

Use example 4

A nematic liquid crystal composition consisting of

20 wt. %

35 wt. %

30 wt. %

15 wt. % was filled in a cell provided with 15 wt.% transparent electrodes each obtained by applying PVA as an aligning agent onto the surface and rubbing the resulting surface to subject it to a parallel aligning treatment and having a distance between the electrodes of 10 μm to prepare a TN type display cell, which was then observed under a polarizing microscope. As a result, formation of a reverse twist domain was observed. To this nematic liquid crystal composition was added the compound of Example 1 of the present invention in an amount of 1.0% by weight, and the resulting composition was similarly observed by means of TN type cell. As a result, no reverse twist domain was formed and uniform nematic phases were observed.

EXAMPLE 28

Use example 5

The compound of Example 4 was added in an amount of 1% by weight to ZLI-1132 manufactured by Merck Company, and with the resulting chiral nematic liquid crystal composition, its chiral pitch was measured according to Cano-Wedge method. The results were as follows:

| Temperature (°C.) | Pitch (μm) |
| --- | --- |
| 20 | 27.7 |
| 30 | 27.8 |
| 40 | 28.0 |
| 50 | 28.5 |
| 60 | 29.0 |

EXAMPLE 29

Use example 6

The compound of Example 13, S-5-octyl-2-(4'-(2''-fluorooctyloxy)phenyl) pyrimidine was added in 1% by weight to ZLI-1132 as in Example 28. With the resulting liquid crystal composition, its chiral pitch was measured as in Example 28. A high negative dependence on temperature was observed.

What we claim is:

1. A 2-substituted-alkyl ether expressed by the formula

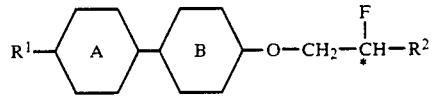

wherein $R^1$ represents linear or branched chain alkyl or alkoxy, each of 5 to 12 carbon atoms, $R^2$ represents linear or branched chain alkyl of 4 to 12 carbon atoms;

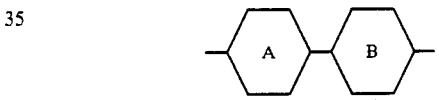

represents

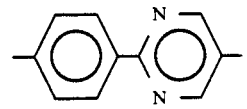

and * indicates an asymmetric carbon atom.

2. A 2-substituted-alkyl ether according to claim 1, wherein $R^1$ represents the alkyl group.

3. A 2-substituted-alkyl ether according to claim 1, wherein $R^2$ is hexyl.

4. A 2-substituted-alkyl ether according to claim 1, wherein $R^2$ is octyl.

5. A 2-substituted-alkyl ether according to claim 1, wherein $R^2$ is isobutyl.

6. A 2-substituted-alkyl ether according to claim 1, wherein $R^1$ represents the alkoxy group.

7. A liquid crystal composition comprising at least two components, at least one of which is a 2-substituted-alkyl ehter as set forth in claim 1.

8. A liquid crystal composition comprising at least two components, at least one of which is a 2-substituted-alkyl ehter as set forth in claim 1, exhibiting chiral smectic phases.

9. A liquid crystal composition comprising at least two components, at least one of which is a 2-substituted-alkyl ehter as set forth in claim 1, exhibiting chiral nematic phases.

* * * * *